United States Patent [19]
Mueller et al.

[11] Patent Number: 5,563,153
[45] Date of Patent: Oct. 8, 1996

[54] STERILE TOPICAL ANESTHETIC GEL

[75] Inventors: David W. Mueller, Mission; James D. Pessetto, Shawnee, both of Kans.

[73] Assignee: University of Kansas Medical Center, Kansas City, Kans.

[21] Appl. No.: 392,045

[22] Filed: Feb. 22, 1995

[51] Int. Cl.$^6$ .......................... A61K 31/44; A61K 31/47; A61K 31/24; A61K 31/195
[52] U.S. Cl. .......................... 514/305; 514/312; 514/535; 514/567; 514/568; 514/617; 514/622; 514/652; 514/653; 514/816; 514/817; 514/818; 514/944
[58] Field of Search ...................... 514/817, 944, 514/535, 617, 568, 312, 305, 622, 652, 653, 567, 816, 818

[56] References Cited

U.S. PATENT DOCUMENTS

| | | | |
|---|---|---|---|
| 4,474,748 | 10/1984 | Sipos | 424/78.07 |
| 4,945,084 | 7/1990 | Packman | 514/53 |
| 5,192,802 | 3/1993 | Rencher | 514/535 |
| 5,196,405 | 3/1993 | Packman | 514/53 |

OTHER PUBLICATIONS

Handbook of Nonprescription Drugs, Eight Ed. 1986, pp. 504–505.

Primary Examiner—John W. Rollins
Attorney, Agent, or Firm—Benjamin Aaron Adler

[57] ABSTRACT

The present invention provides a topical anesthetic gel composition, comprising: (a) one or more topical anesthetic agents; (b) an adrenergic sympathomimetic compound; and (c) a pharmaceutical gel component. The present invention also provides a topical anesthetic gel composition, comprising: (a) tetracaine HCl, wherein said tetracaine HCl is contained in said composition in an amount of from about 0.01% to about 1.0% by weight, based upon the total weight of said composition; (b) epinephrine HCl topical solution, wherein said epinephrine HCl is contained in said composition in an amount of from about 0.04% to about 0.1% by weight, based upon the total weight of said composition; (c) cocaine HCl, wherein said cocaine HCl is contained in said composition in an amount of from about 3.0% to about 12.0% by weight, based upon the total weight of said composition; and (d) GELFOAM®, wherein said Gelfoam® is contained in said composition in an amount of from about 6.0% to about 9.0% by weight, based upon the total weight of said composition. Further provided are other topical anesthetic compositions.

5 Claims, No Drawings

STERILE TOPICAL ANESTHETIC GEL

BACKGROUND OF THE INVENTION

1. Field of the Invention

The present invention relates generally to the field of production and formulation of pharmaceuticals. More specifically, the present invention relates to a novel pharmaceutical formulation of a combination of topical anesthetics.

2. Description of the Related Art

Topical anesthetic compositions are generally well known. For example, U.S. Pat. No. 2,004,891 to Goldberg teaches an anesthetic solution containing procaine acetate and epinephrine HCl. U.S. Pat. No. 3,038,835 to Endres et al. discloses derivatives of 2,6-xylidine as a surface anesthetic. Similarly, RESOLVE™ is a commercially available product that produces surface anesthesia when applied topically to inflamed or abraded skin or to mucous membranes.

Topical anesthetic compositions such as tetracaine-adrenaline-cocaine are considered safe and effective. It has been considered beneficial in the art to have a more viscous topical preparation that could be directly applied onto the wound surface so as to be able to use a minimal volume and dosage of the pharmaceuticals and to remain in contact with the lacerated tissue of interest without running off onto mucosal or ocular surfaces.

There are several known disadvantages associated with the application of conventional topical anesthetic medications. For example, the medicine must be applied to and saturate a cotton ball or similar applicator which tends to absorb most of the medicine. This drawback has prompted the use of a much larger volume of medication which necessarily increases the cost of a unit dose of medication and possible over-exposure to certain components, e.g., cocaine. In addition, the medication-saturated applicator may not remain in direct contact with the entire wound surface leading to inadequate areas of anesthesia. Furthermore, it may be difficult to secure an applicator to certain body areas, such as a head wound and a mainly liquid topical anesthetic could easily run off the applicator and irritate ocular or mucosal surfaces.

Bonadio and Wagner (Annals of Emergency Medicine, 21:1435–1438, December 1992) describe an adrenalin-cocaine gel topical anesthetic for children. Unfortunately, the topical anesthetic composition of Bonadio and Wagner was not sterile. The prior art is deficient in the lack of sterile topical anesthetic gel formulation which has superior properties and actions. The present invention fulfills this longstanding need and desire in the art.

SUMMARY OF THE INVENTION

In one embodiment of the present invention, there is provided a topical anesthetic gel composition, comprising: (a) one or more topical anesthetic agents; and (b) a pharmaceutical gel component. In a preferred embodiment, the topical anesthetic gel composition further comprises an adrenergic sympathomimetic compound.

In another embodiment of the present invention, there is provided a topical anesthetic gel composition, comprising: (a) tetracaine HCl, wherein said tetracaine HCl is contained in said composition in an amount of from about 0.01% to about 1.0% by weight, based upon the total weight of said composition; (b) epinephrine HCl topical solution, wherein said epinephrine HCl is contained in said composition in an amount of from about 0.04% to about 0.1% by weight, based upon the total weight of said composition; (c) cocaine HCl, wherein said cocaine HCl is contained in said composition in an amount of from about 3.0% to about 12.0% by weight, based upon the total weight of said composition; and (d) GELFOAM®, wherein said GELFOAM® is contained in said composition in an amount of from about 6.0% to about 9.0% by weight, based upon the total weight of said composition.

In yet another embodiment of the present invention, there is provided a topical anesthetic gel composition, comprising: (a) lidocaine HCl, wherein said lidocaine HCl is contained in said composition in an amount of from about 0.9% to about 30% by weight, based upon the total weight of said composition; (b) epinephrine HCl topical solution, wherein said epinephrine HCl is contained in said composition in an amount of from about 0.04% to about 0.1% by weight, based upon the total weight of said composition; (c) tetracaine HCl, wherein said tetracaine HCl is contained in said composition in an amount of from about 0.01% to about 1.0% by weight, based upon the total weight of said composition; and (d) GELFOAM®, wherein said GELFOAM® is contained in said composition in an amount of from about 6.0% to about 9.0% by weight, based upon the total weight of said composition.

In yet another embodiment of the present invention, there is provided a topical anesthetic gel composition, comprising: (a) lidocaine HCl, wherein said lidocaine HCl is contained in said composition in an amount of from about 0.9% to about 30% by weight, based upon the total weight of said composition; and (b) GELFOAM®, wherein said GELFOAM® is contained in said composition in an amount of from about 6.0% to about 9.0% by weight, based upon the total weight of said composition.

Other and further aspects, features, and advantages of the present invention will be apparent from the following description of the presently preferred embodiments of the invention given for the purpose of disclosure.

DETAILED DESCRIPTION OF THE INVENTION

The present invention is directed to a composition of matter comprising a topical anesthetic gel composition, comprising: (a) one or more topical anesthetic agents; (b) an adrenergic sympathomimetic compound; and (c) a pharmaceutical gel component.

In a preferred embodiment, the sterile pharmaceutical formulation of the present invention comprises a gel mixture. Preferably, the gel mixture is GELFOAM®, brand of absorbable gelatin sterile powder, hereinafter referred to as GELFOAM®. GELFOAM® is manufactured by the Upjohn Corporation and is an absorbable gelatin powder milled from absorbable gelatin sponge, USP. The sterile pharmaceutical formulation of the present invention can be prepared in a sterile fashion into a gel-like substance that has the consistency of horseradish sauce. The methylcellulose-based gel has a consistency more similar to old, partially dried gelatin. The sterile topical anesthetic preparation of the present invention may be easily mixed, measured, and stored in a sterile manner. It also has the hemostatic properties necessary to assist in preparation of the wound for repair.

The "effective amount" or "pharmacologically effective amount" of a local anesthetic in a unit dose of the composition of the present invention depends on a number of factors. Included among these factors is the quantity of the gelling compound used and the tolerance of the active ingredient of anesthetic. The effective amount of local anesthetic ranges from about 0.5% to about 30% by weight based on the total weight of the final formulation. Ranges of representative topical anesthetics are given in TABLE I.

TABLE I

| Representative Topical Anesthetics | |
| --- | --- |
| lidocaine HCl | 0.5–30 weight percent |
| dyclonine HCl | 0.5–3 weight percent |
| pramoxine HCl | 0.5–3 weight percent |
| benzocaine | 0.5–25 weight percent |
| tetracaine HCl | 0.5–3 weight percent |
| dibucaine HCl | 0.2–2 weight percent |
| lidocaine base | 0.5–30 weight percent |
| cocaine HCl | 2–20 weight percent |

In the topical anesthetic preparations described by the present invention, the gel component of the preparation should have certain properties. For example, the product should have certain "tackiness" to cling to the site of application. Secondly, the gel component should be easily removed by saline irrigation without leaving any residue. Further, it is preferably that the gel component have surface contact/release characteristics which allow for good surface adhesion which allows for uniform release of the medications from the gel. It is specifically contemplated that other gelatin formulations, e.g., types I–IV collagen preparations, could be used by those having ordinary skill in this art. Taken together, the desirable characteristics of a useful gel component of the compositions of the present invention include (1) water solubility, (2) sterilizable, (3) inert carrier, i.e., pH and osmolality is such that the gel is relatively inert, and (4) ease of manipulation.

Generally, the gel component of the topical anesthetic preparations of the present invention is contained in the formulation is a concentration of from about 1.0% to about 15% Preferably, the gel component is contained in the composition is a concentration of from about 6.0% to about 9.0%.

Other agents may be added to the composition to impart additional desirable properties. Thus, for example, a vehicle and/or a humectant may be used. A typical vehicle includes water or sodium chloride (0.9%) for irrigation (normal saline). It is usually added to make up the weight or volume.

The following examples are given for the purpose of illustrating various embodiments of the invention and are not meant to limit the present invention in any fashion.

EXAMPLE 1

In one embodiment of the present invention, the topical anesthetic preparation of the present invention has the following ingredients: (1) tetracaine HCl, 0.195 g; (2) ADRENALIN® topical solution 1:1000 (19.5 ml); (3) cocaine HCl, 4.60 grams; (4) NaCl 0.9% for irrigation, qsad 39 ml; (5) one MILLEX®-GS 0.2 micron filter; and (6) GELFOAM® powder, 3×1 gram. Using aseptic technique, all sterile manipulations are performed in the laminar airflow hood. First, ADRENALIN® solution was measured and placed in a pyrogen free 50 ml beaker. The tetracaine HCl and cocaine HCl powders were weighed and added to the beaker and the beaker was mixed well. The solution was returned to graduate and QSAD to volume with a 0.9% saline solution for irrigation. The solution was returned to the beaker and mixed well. In a laminar airflow hood (LAF) hood, the entire volume was drawn up in a syringe. A MILLEX®-GS 0.2 micron filter was attached to the syringe. 12 ml of the topical anesthetic solution was dispensed into each of the 1 gram jars of GELFOAM®. Using the wooden end of a sterile swab stick or similar sterile stirring instrument, the solution was stirred until a uniform distribution was reached. Using a sterile 2.5 ml measuring spoon, 2.5 ml of gel was dispensed into each of the previously sterilized and de-pyrogenated amber glass bottle (15 ml). A sterile lid was carefully placed on each bottle. Using an electric capper, each vial was capped with an tamper proof aluminum lid and checked for a tight seal. The topical anesthetic preparation of the present invention has a shelf life of approximately 3 months in this embodiment. This formulation of the topical anesthetic preparation of the present invention has the following concentrations: tetracaine, 0.5%; ADRENALIN®, 1:2,000; and cocaine, 11.8%. Each batch was tested for sterility using trypsin soy broth and nutrient agar streak plates. The final product in amber vials should be protected from light to prevent the epinephrine HCl from oxidizing and breaking down.

Use of the topical gel anesthetic preparation of the present invention produced excellent anesthesia and vasoconstriction after approximately 15 minutes of application. The topical anesthetic gel preparation is removed out of the container with the sterile fabric end of an applicator and applied to the wound. The wound was covered with a dry, sterile 2×2 inch gauze square and tape. Within 15 minutes, the edges were blanched and anesthetized. Wound repair occurred with virtually 100% successful anesthesia present. The gel appeared to "melt" when it entered the wound and was easily irrigated away. No complications were observed and the preparation did not drip or run into eyes or the mouth. In a very small percentage of the cases, it may be necessary to have an additional injection of buffered lidocaine. Alternatively, the novel anesthetic gel compositions of the present invention need not be rinsed out of the site of application. For example, the anesthetic gels could simply be left in the site of application to continue producing the pharmacological effects.

EXAMPLE 2

In another embodiment of the present invention, the topical anesthetic preparation of the present invention has the following ingredients: (1) lidocaine HCl, 9 ml of a 4% topical solution; (2) ADRENALIN® topical solution 1:1000 (18 ml); (3) tetracaine, 9 ml of a 2% topical solution; and (4) GELFOAM® powder, 3×1 gram. Using aseptic technique, all sterile manipulations are performed in the laminar airflow hood. First, ADRENALIN® solution was measured and placed in a pyrogen free 50 ml beaker. The tetracaine HCl and lidocaine HCl powders were weighed and added to the beaker and the beaker was mixed well. The solution was returned to graduate and QSAD to volume with NaCl 0.9% for irrigation. The solution was returned to the beaker and mixed well. In a LAF hood, the entire volume was drawn up in a syringe. A MILLEX®-GS 0.2 micron filter was attached to the syringe. 12 ml of the topical anesthetic solution was dispensed into each 1 gram jar of GELFOAM®.

Using the wooden end of a sterile swab stick or similar sterile stirring instrument, the solution was stirred until a uniform distribution was reached. The plunger was removed from a 60 ml syringe and set down with care taken not to contaminate the plunger. Using a Leur Lock to Oral Slip connector, a 3 ml Oral Syringe was attached to the syringe. Using a measuring spoon, all of the lidocaine gel was transferred into the syringe. The plunger was reinserted and the air was removed from the syringes. Each 3 ml Oral Syringe was filled with 2 ml of the lidocaine/epinephrine HCl/tetracaine gel anesthetic of the present invention.

EXAMPLE 3

In another embodiment of the present invention, the topical anesthetic preparation of the present invention has the following ingredients: (1) lidocaine HCl, 2.4 grams; (2) sterile water for irrigation, qsad 12 ml; and (4) GELFOAM® powder, 1 gram. The lidocaine was weighed and dissolved in 8 ml of sterile water for irrigation in a mortar. Lidocaine HCl is soluble at approximately 1 gm per 0.7 ml of water. The solution was QSAD to 12 ml with sterile water for irrigation to yield a 20% lidocaine HCl solution. The 12 ml of lidocaine 20% solution was added to a 1 g jar of GELFOAM® powder. Using a sterile stirring device, the solution was stirred until a uniform distribution was reached. The plunger was removed from a 20 ml syringe and set down with care taken not to contaminate the plunger. Using a Leur Lock to Oral Slip connector, a 3 ml Oral Syringe was attached to the syringe. All of the lidocaine gel was transferred in a sterile manner into the syringe. The plunger was reinserted and the air was removed from the syringes. Each 3 ml Oral Syringe was filled with 1 ml of the lidocaine gel anesthetic of the present invention.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A topical anesthetic gel composition comprising,
   (a) one or more topical anesthetic agents; and
   (b) a pharmaceutical gel component, wherein said pharmaceutical gel component is Gelfoam®.

2. The composition of claim 1, wherein said Gelfoam® is contained in said composition in an amount of from about 6.0% to about 9.0% by weight, based upon the total weight of said composition.

3. A topical anesthetic gel composition, comprising:
   (a) tetracaine HCl, wherein said tetracaine HCl is contained in said composition in an amount of from about 0.01% to about 1.0% by weight, based upon the total weight of said composition;
   (b) epinephrine HCl topical solution, wherein said epinephrine HCl is contained in said composition in an amount of from about 0.04% to about 0.1% by weight, based upon the total weight of said composition;
   (c) cocaine HCl, wherein said cocaine HCl is contained in said composition in an amount of from about 3.0% to about 12.0% by weight, based upon the total weight of said composition; and
   (d) GELFOAM®, wherein said GELFOAM® is contained in said composition in an amount of from about 6.0% to about 9.0% by weight, based upon the total weight of said composition.

4. A topical anesthetic gel composition, comprising:
   (a) lidocaine HCl, wherein said lidocaine HCl is contained in said composition in an amount of from about 0.9% to about 30% by weight, based upon the total weight of said composition;
   (b) epinephrine HCl topical solution, wherein said epinephrine HCl is contained in said composition in an amount of from about 0.04% to about 0.1% by weight, based upon the total weight of said composition;
   (c) tetracaine HCl, wherein said tetracaine HCl is contained in said composition in an amount of from about 0.01% to about 1.0% by weight, based upon the total weight of said composition; and
   (d) GELFOAM®, wherein said GELFOAM® is contained in said composition in an amount of from about 6.0% to about 9.0% by weight, based upon the total weight of said composition.

5. A topical anesthetic gel composition, comprising:
   (a) lidocaine HCl, wherein said lidocaine HCl is contained in said composition in an amount of from about 0.9% to about 30% by weight, based upon the total weight of said composition; and
   (b) GELFOAM®, wherein said GELFOAM® is contained in said composition in an amount of from about 6.0% to about 9.0% by weight, based upon the total weight of said composition.

\* \* \* \* \*